United States Patent
Nakayama et al.

(10) Patent No.: US 9,637,421 B2
(45) Date of Patent: May 2, 2017

(54) METHOD FOR PRODUCING OCTADIENE

(71) Applicant: KURARAY CO., LTD., Kurashiki-shi (JP)

(72) Inventors: Osamu Nakayama, Kamisu (JP); Junichi Fuji, Suginami-ku (JP); Masaki Shimizu, Kamisu (JP)

(73) Assignee: KURARAY CO., LTD., Kurashiki-shi (JP)

( * ) Notice: Subject to any disclaimer, the term of this patent is extended or adjusted under 35 U.S.C. 154(b) by 115 days.

(21) Appl. No.: 14/401,680

(22) PCT Filed: May 15, 2013

(86) PCT No.: PCT/JP2013/063595
§ 371 (c)(1),
(2) Date: Nov. 17, 2014

(87) PCT Pub. No.: WO2013/172389
PCT Pub. Date: Nov. 21, 2013

(65) Prior Publication Data
US 2015/0105598 A1 Apr. 16, 2015

(30) Foreign Application Priority Data
May 17, 2012 (JP) ................................. 2012-113193

(51) Int. Cl.
*C07C 1/20* (2006.01)
*C07C 1/207* (2006.01)
*C07C 1/213* (2006.01)
*B01J 31/24* (2006.01)

(52) U.S. Cl.
CPC ............. *C07C 1/2078* (2013.01); *B01J 31/24* (2013.01); *B01J 31/2404* (2013.01); *C07C 1/213* (2013.01); *B01J 2231/40* (2013.01); *B01J 2531/824* (2013.01); *C07C 2531/12* (2013.01); *C07C 2531/24* (2013.01)

(58) Field of Classification Search
None
See application file for complete search history.

(56) References Cited

U.S. PATENT DOCUMENTS 5,763,718 A * 6/1998 Tsuda .................. C07C 2/74
585/368
2012/0029229 A1* 2/2012 Miyoshi .................. C07C 7/005
560/218

FOREIGN PATENT DOCUMENTS

| CN | 102369173 A | 3/2012 |
|----|----|----|
| JP | 47 17703 | 9/1972 |
| JP | 5 238964 | 9/1993 |
| JP | 6 40954 | 2/1994 |
| JP | 2003342202 A * | 12/2003 |
| WO | 2010 113531 | 10/2010 |

OTHER PUBLICATIONS

English Translation of JP2003342202 retrieved from EPO May 3, 2016.*
Fisher Science, Arcos Organics, Safety Data Sheet of Bis(2-methyoxyethyl)ether, Fisher Scientific, Jan. 7, 2015).*
Combined Office Action and Search Report issued Jul. 27, 2015 in Chinese Patent Application No. 201380025815.9 (with English translation of Category of Cited Documents).
Jiro Tsuji, et al., "Preparation of 1-Alkenes by the Palladium-Catalyzed Hydrogenolysis of Terminal Allylic Carbonates and Acetates with Formic Acid-Triethylamine" Synthesis, Aug. 1986, pp. 623-627.
Jiro Tsuji, "Selectivities in organic reactions via π-allylpalladium complexes" Pure and Applied Chemistry, vol. 61, No. 10, 1989, pp. 1673-1680.
Jiro Tsuji, et al., "Regioselective synthesis of 1-olefins by palladium-catalyzed hydrogenolysis of terminal allylic compounds with ammonium formate", Chemistry Letter, vol. 6, pp. 1017-1020, (1984).
Jiro Tsuji, et al., "A convenient method for the preparation of 1-olefins by the palladium catalyzed hydrogenolysis of allylic acetates and allylic phenyl ethers with ammonium formate", Tetrahedron Letters, vol. 7, pp. 613-616, (1979).
Masato Oshima, et al., "Synthesis and Properties of (n3-1-Methylally)palladium (II) Formates as Models of Intermediates in the Palladium-Catalyzed Reductive Cleavage of Allylic Carboxylates and Carbonates with Formic Acid", Bull. Chem. Soc. Jpn., vol. 73, pp. 453-464, (2000).
International Search Report Issued Aug. 20, 2013 in PCT/JP13/063595 Filed May 15, 2013.

* cited by examiner

*Primary Examiner* — In Suk Bullock
*Assistant Examiner* — Philip Louie
(74) *Attorney, Agent, or Firm* — Oblon, McClelland, Maier & Neustadt, L.L.P.

(57) ABSTRACT

An object of the present invention is to provide a process for producing an octadiene from 2,7-octadienyl formate in an industrially useful manner in which palladium can maintain its catalytic activity for a long period of time. More specifically, the present invention relates to a process for producing an octadiene which includes the steps of continuously adding 2,7-octadienyl formate into a reaction system in which a mixture of a palladium compound, a tertiary organophosphorus compound and a solvent is present; and subjecting the 2,7-octadienyl formate to reaction while continuously distilling off a reaction product containing the resulting octadiene out of the reaction system.

6 Claims, No Drawings

METHOD FOR PRODUCING OCTADIENE

TECHNICAL FIELD

The present invention relates to a process for producing an octadiene (which is intended herein to include 1,7-octadiene and 1,6-octadiene; hereinafter also defined in the same way). The octadiene obtained by the process of the present invention is important as a crosslinking agent or a modifying agent used upon production of polyolefins as well as an intermediate product for synthesis of sebacic acid, C10 diols or C10 diamines. In addition, the sebacic acid, C10 diols or C10 diamines are useful as raw materials for polyesters, polyamides, alkyd resins and plasticizers.

BACKGROUND ART

As the process for producing an octadiene using 2,7-octadienyl formate as a raw material, in Synthesis Example 3 of PTL1, there is described the process in which a mixed solution prepared by allowing palladium acetate and tricyclohexyl phosphine to be present in diglyme (diethylene glycol dimethyl ether) is heated to 120° C., and formylated 2,7-octadien-1-ol (=2,7-octadienyl formate) is added dropwise thereto and reacted therewith to obtain crude 1,7-octadiene (1,7-octadiene/1,6-octadiene=95.4/4.5). Also, in NPTL1, it is described that 2,7-octadienyl formate is reacted in the presence of a palladium compound and an organophosphorus compound to thereby obtain an octadiene, though there is no description concerning a yield of the octadiene. On the other hand, PTL2 discloses a method for producing a propene derivative by acting a palladium compound on a formic acid ester.

CITATION LIST

Patent Literature

PTL1: PCT Pamphlet WO 2010/113531A
PTL2: JP 6-40954A

Non-Patent Literature

NPTL1: Bulletin of the Chemical Society of Japan, Vol. 73, 453-464 (2000)

In Synthesis Example 3 of PTL1, there is no description concerning the technology of using expensive palladium in the reaction in an industrially useful manner while maintaining a catalytic activity of the palladium for a long period of time. In NPTL1, there is no description concerning a yield of the octadiene as described above, and further the palladium compound is used in an amount as large as 25 mmol equivalent based on the 2,7-octadienyl formate, and therefore NPTL1 fails to provide an economically advantageous process from the industrial viewpoints. Thus, the process of NPTL1 is immediately impracticable. In PTL2, it is described that the reaction is preferably carried out in the presence of a base, but there is no concrete description concerning any advantageous effects thereof.

SUMMARY OF INVENTION

Technical Problem

Thus, an object of the present invention is to provide a process for producing an octadiene from 2,7-octadienyl formate in an industrially useful manner in which palladium can maintain its catalytic activity for a long period of time.

Solution to Problem

In accordance with the present invention, the above object can be achieved by the following aspects of the present invention.

(1) A process for producing an octadiene including the steps of:
continuously adding 2,7-octadienyl formate into a reaction system in which a mixture of a palladium compound, a tertiary organophosphorus compound and a solvent is present; and
subjecting the 2,7-octadienyl formate to reaction while continuously distilling off a reaction product containing the resulting octadiene out of the reaction system.

(2) A process for producing an octadiene including the steps of:
continuously adding 2,7-octadienyl formate into a reaction system in which a mixture of a palladium compound, a tertiary organophosphorus compound, a tertiary amine and a solvent is present; and
subjecting the 2,7-octadienyl formate to reaction while continuously distilling off a reaction product containing the resulting octadiene out of the reaction system.

(3) The process for producing an octadiene according to the above aspect (2), wherein the tertiary amine is used in an amount of from 0.0001 to 95% by mass on the basis of a total amount of the mixture of the palladium compound, the tertiary organophosphorus compound, the tertiary amine and the solvent which is present in the reaction system.

(4) The process for producing an octadiene according to the above aspect (2) or (3), wherein the tertiary amine has a boiling point higher than that of the octadiene as measured under atmospheric pressure.

(5) The process for producing an octadiene according to any one of the above aspects (1) to (4), wherein the tertiary organophosphorus compound is used in an amount of from 4 to 10,000 times by mol, on the basis of a palladium atom contained in the palladium compound.

(6) The process for producing an octadiene according to any one of the above aspects (1) to (5), wherein the solvent has a boiling point higher than that of the octadiene as measured under atmospheric pressure.

(7) The process for producing an octadiene according to the above aspect (6), wherein the solvent used in the process is an ether-based solvent.

Advantageous Effects of Invention

According to the present invention, upon producing an octadiene from 2,7-octadienyl formate, it is possible to produce the octadiene in an industrially useful manner while maintaining a catalytic activity of palladium for a long period of time. In addition, when a tertiary amine is further allowed to be present in a specific amount on the basis of a mixture of a palladium compound, a tertiary organophosphorus compound and a solvent which is present in a reaction system, it is possible to drastically increase a time period capable of maintaining a catalytic activity of the palladium used in the process of the present invention.

DESCRIPTION OF EMBODIMENTS

The process of the present invention is carried out by a continuous reaction method. More specifically, 2,7-octadienyl formate is continuously added to a reaction system in which a mixture of a palladium compound, a tertiary organophosphorus compound and a solvent which preferably further contains a tertiary amine is present, and the 2,7-octadienyl formate is subjected to reaction while continuously distilling off a reaction product containing the resulting octadiene out of the reaction system.

The 2,7-octadienyl formate used as a raw material in the process of the present invention may be readily produced by reacting 2,7-octadien-1-ol with formic acid.

Examples of the palladium compound used in the process of the present invention include palladium acetate, palladium acetyl acetonate, palladium chloride, tetrakis(triphenyl phosphine) palladium, dichlorobis(benzonitrile) palladium and tris(dibenzylidene acetone) dipalladium. These palladium compounds may be used alone or in combination of any two or more thereof. The amount of the palladium compound used in the reaction is not strictly limited. However, from the economical viewpoints, the palladium compound is preferably used in such an amount that a concentration of palladium in the reaction system in which a mixture of the palladium compound, the tertiary organophosphorus compound and the solvent which preferably further contains the tertiary amine is present falls within the range of from 0.00001 to 10 mmol/L.

Examples of the tertiary organophosphorus compound used in the process of the present invention include monodentate phosphines such as triisopropyl phosphine, tri-n-butyl phosphine, tri-t-butyl phosphine, tri-n-octyl phosphine, tricyclohexyl phosphine, tribenzyl phosphine, t-butyl diphenyl phosphine, cyclohexyl diphenyl phosphine, triphenyl phosphine, tri(o-tolyl) phosphine, tri(2,6-dimethoxyphenyl) phosphine and tris(diethylaminophenyl) phosphine; multidentate phosphines such as 1,2-bis(diphenyl phosphino)ethane, 1,3-bis(diphenyl phosphino)propane, 1,4-bis(diphenyl phosphino)butane and 1,6-bis(diphenyl phosphino) hexane; phosphites such as triisopropyl phosphite, tri-n-butyl phosphite, tri-t-butyl phosphite, triphenyl phosphite and tris(2-methylphenyl)phosphite; and the like.

The tertiary organophosphorus compound is preferably used in an amount of from 4 to 10,000 times by mol, more preferably from 4 to 5,000 times by mol, still more preferably from 8 to 1,000 times by mol, and even still more preferably from 15 to 500 times by mol, on the basis of a palladium atom contained in the palladium compound, from the viewpoint of ensuring a stability of a catalyst composition containing the palladium compound together.

In the process of the present invention, as the reaction is continuously carried out for a prolonged period of time, at least a part of the tertiary organophosphorus compound is oxidized in the reaction system, so that there is such a tendency that the catalyst composition constituted of the palladium compound and the tertiary organophosphorus compound is deteriorated in catalytic activity thereof. For this reason, when practicing the process of the present invention, it is preferred that the tertiary organophosphorus compound is intermittently or continuously added in an appropriate amount corresponding to an amount of the tertiary organophosphorus compound reduced by the oxidation to the reaction system. Meanwhile, the amount of the tertiary organophosphorus compound reduced in the reaction system may be determined by subjecting a part of the reaction solution sampled from the reaction system to gas chromatography.

The method of adding the above tertiary organophosphorus compound is not particularly limited, and the tertiary organophosphorus compound may be added to the reaction system in either an intermittent or continuous manner. The amount of the tertiary organophosphorus compound added is preferably controlled such that the amount of the tertiary organophosphorus compound being present in the reaction system is from 4 to 10,000 times by mol, more preferably from 4 to 5,000 times by mol, still more preferably from 8 to 1,000 times by mol, and even still more preferably from 15 to 500 times by mol, on the basis of a palladium atom contained in the palladium compound.

In the process of the present invention, it is preferred to continuously add 2,7-octadienyl formate into the reaction system in which a mixture of the palladium compound, the tertiary organophosphorus compound and the solvent which preferably further contains the tertiary amine is present; and subjecting the 2,7-octadienyl formate to reaction while continuously distilling off a reaction product containing the resulting octadiene out of the reaction system. When the tertiary amine is allowed to be present in the reaction system, it is possible to drastically increase a time period capable of maintaining a catalytic activity of the catalyst composition constituted of the palladium compound and the tertiary organophosphorus compound, and carry out the continuous reaction for a still longer period of time.

The tertiary amine used in the process of the present invention extremely preferably has a boiling point higher than that of the octadiene as measured under atmospheric pressure from the viewpoint of facilitated separation of the tertiary amine from the octadiene as the reaction product. More specifically, the boiling point of the tertiary amine as measured under atmospheric pressure is preferably higher by 15° C. or more, more preferably higher by 30° C. or more, and still more preferably higher by 50° C. or more, than the boiling point of the octadiene. Examples of the tertiary amine having the above boiling point include monoamines such as N-methyl dibutylamine, tributylamine, triisobutylamine, tripentylamine, N,N-dimethyl hexylamine, trihexylamine, N,N-dimethyl octylamine, N-methyl dioctylamine, trioctylamine, triisooctylamine, N,N-dimethyl dodecylamine, tridecylamine, triisodecylamine, N,N-dimethyl benzylamine, N,N-dimethyl myristylamine, N,N-dimethyl palmitylamine, N,N-dimethyl stearylamine and N,N-dimethyl aniline; diamines such as dipiperidinomethane, N,N,N',N'-tetramethyl-1,6-hexanediamine and N,N,N',N'-tetraethyl-1,3-propanediamine; triamines such as N,N,N',N'',N''-pentamethyl diethylene triamine; tetramines such as 1,1,4,7,10,10-hexamethyl triethylene tetramine; heterocyclic amines such as 1-phenyl pyrrole. These tertiary amines may be used alone or in combination of any two or more thereof.

The amount of the tertiary amine, if used, is usually in the range of from 0.0001 to 95% by mass, preferably from 0.001 to 80% by mass, and more preferably from 0.01 to 50% by mass on the basis of a total amount of the mixture of the palladium compound, the tertiary organophosphorus compound, the tertiary amine and the solvent which is present in the reaction system, from the viewpoints of increasing a time period capable of maintaining a catalytic activity of the catalyst composition constituted of the palladium compound and the tertiary organophosphorus compound, etc.

The process of the present invention is carried out in the presence of the solvent. When using no solvent in the process, the catalyst composition constituted of the palladium compound and the tertiary organophosphorus compound tends to be hardly stabilized, so that it may be difficult to continue the reaction for a long period of time. The solvent used in the process of the present invention extremely preferably has a boiling point higher than that of the octadiene as measured under atmospheric pressure from the viewpoint of facilitated separation of the solvent from the octadiene as the reaction product. More specifically, the boiling point of the solvent as measured under atmospheric pressure is preferably higher by 15° C. or more, more preferably higher by 30° C. or more, and still more preferably higher by 50° C. or more, than the boiling point of the octadiene.

Examples of the solvent having the above boiling point include aliphatic hydrocarbons such as dodecane; aromatic hydrocarbons such as xylene, mesitylene and tetrahydronaphthalene; ketones such as 2-octanone and cyclohexanone; ethers such as ethylene glycol dibutyl ether, diethylene glycol dimethyl ether, diethylene glycol diethyl ether, triethylene glycol dimethyl ether and tetraethylene glycol dimethyl ether; monoether monoesters such as ethylene glycol monobutyl ether acetate; aliphatic or aromatic polyvalent esters such as dimethyl adipate, dimethyl phthalate and dioctyl phthalate; aromatic nitro compounds such as nitrobenzene; nitriles such as benzonitrile; amides such as N,N-dimethylformamide, N,N-dimethylacetamide and N-methyl pyrrolidone; and 1,3-dimethyl-2-imidazolidinone, dimethyl sulfoxide, sulfolane and methyl sulfolane, etc. These solvents may be used alone or in combination of any two or more thereof. Of these solvents, from the viewpoint of allowing the reaction to proceed smoothly, the ethers such as ethylene glycol dibutyl ether, diethylene glycol dimethyl ether, diethylene glycol diethyl ether, triethylene glycol dimethyl ether and tetraethylene glycol dimethyl ether are preferably used.

The amount of the solvent used in the reaction is usually in the range of from 10 to 90% by mass, preferably from 20 to 80% by mass, and more preferably from 30 to 70% by mass on the basis of a total amount of the mixture of the palladium compound, the tertiary organophosphorus compound and the solvent which preferably further contains the tertiary amine.

In the process of the present invention, the reaction temperature is usually preferably in the range of from 80 to 170° C. The reaction temperature is more preferably in the range of from 100 to 145° C. from the viewpoints of a high reaction rate and a good stability of the catalyst composition constituted of the palladium compound and the tertiary organophosphorus compound. When the reaction temperature is lower than 80° C., the reaction rate tends to be lowered. On the other hand, when the reaction temperature is higher than 170° C., the catalyst composition constituted of the palladium compound and the tertiary organophosphorus compound tends to suffer from decomposition.

In the process of the present invention, from the viewpoint of conducting the reaction while continuously distilling off the reaction product containing the octadiene out of the reaction system, the reaction pressure is usually preferably in the range of from 4 kPa to atmospheric pressure as measured at the reaction temperature ranging from 80 to 170° C., and more preferably in the range of from 20 kPa to 55 kPa as measured at the reaction temperature ranging from 100 to 145° C. Also, in the process of the present invention, from the viewpoint of suppressing oxidation of the tertiary organophosphorus compound, the reaction is preferably carried out in an atmosphere of a gas inert to the reaction, such as nitrogen and argon.

In the process of the present invention, 2,7-octadienyl formate is continuously added to the reaction system in which the mixture of the palladium compound, the tertiary organophosphorus compound and the solvent which preferably further contains the tertiary amine is present, and the 2,7-octadienyl formate is subjected to reaction while continuously distilling off the reaction product containing the octadiene (which further contains 1,3,7-octatriene and other low-boiling byproducts, and may also be hereinafter generally referred to as a "reaction distillate mixed solution") out of the reaction system. When the reaction distillate mixed solution is subjected to ordinary purification treatments for organic compounds such as rectification, it is possible to enhance a purity of 1,7-octadiene or 1,6-octadiene as an aimed product.

EXAMPLES

The present invention is described in more detail below by referring to the following examples. It should be noted, however, that the following examples are only illustrative and not intended to limit the invention thereto.

Measuring Conditions of Gas Chromatography (GC)

The mixed solution present in the reaction system was subjected to GC analysis under the following conditions.
Analyzer: "GC14A" (available from Shimadzu Corp.)
Detector: "FID" (hydrogen flame ionization detector)
Column Used: "G-100" (available from a general incorporated foundation "Chemicals Evaluation and Research Institute, Japan")
Analyzing Conditions: Injection Temp.: 270° C.
Detection Temp.: 270° C.
Heating Conditions: 100° C. (0 min)→heated at 10° C./min→270° C.

In addition, the GC analysis of the reaction distillate mixed solution was conducted under the following conditions.
Analyzer: "GC14A" (available from Shimadzu Corp.)
Detector: "FID" (hydrogen flame ionization detector)
Column Used: "CBP-1" (available from Shimadzu Corp.)
Analyzing Conditions: Injection Temp.: 270° C.
Detection Temp.: 270° C.
Heating Conditions: 60° C. (15 min)→heated at 20° C./min→260° C.

Example 1

A 6 m³ reaction vessel was charged with 2,503 L (2,365 kg) of diethylene glycol dimethyl ether, 40.0 g (0.18 mol) of palladium acetate and 3.0 kg of a 20% by mass tricyclohexyl phosphine-o-xylene solution (1.9 mol in terms of tricyclohexyl phosphine), and the reaction pressure in the reaction vessel was reduced to 40 kPa and the reaction temperature therein was raised to 120° C. At the time at which an inside temperature of the reaction vessel reached 120° C., 2,7-octadienyl formate and a 20% by mass tricyclohexyl phosphine-o-xylene solution were added thereto at feed rates of 103.3 kg/h and 0.73 kg/h, respectively, using a feed pump. When the reaction was conducted while distilling off a reaction product containing the resulting octadiene out of the reaction system, it was possible to continue the reaction for 85 h. When the reaction was further continued, an amount of a reaction distillate mixed solution produced was gradually reduced, and it was therefore judged that the catalyst composition constituted of the palladium compound and the tertiary organophosphorus compound was deteriorated in catalytic activity thereof. Total amounts of the 2,7-octadienyl formate and 20% by mass tricyclohexyl phosphine-o-xylene solution added in the continuous reaction for 85 h were 8,780 kg (57.0 kmol) and 62.0 kg (39.9 mol in terms of tricyclohexyl phosphine), respectively. Also, a total amount of the resulting reaction distillate mixed solution was 5,897 kg, and a yield of the octadiene was 94.0%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 95/5. (Boiling points under atmospheric pressure were 162° C. for diethylene glycol dimethyl ether; 144° C. for o-xylene; 209° C. for 2,7-octadienyl formate; 117° C. for 1,7-octadiene; and 121° C. for 1,6-octadiene.)

Example 2

A 10 m³ reaction vessel was charged with 3,513 L (3,320 kg) of diethylene glycol dimethyl ether, 60.0 g (0.27 mol) of palladium acetate, 9.0 kg of a 20% by mass tricyclohexyl phosphine-o-xylene solution (5.8 mol in terms of tricyclohexyl phosphine) and 10.0 kg (28.3 mol) of trioctylamine, and the reaction pressure in the reaction vessel was reduced to 50 kPa and the reaction temperature therein was raised to 120° C. At the time at which an inside temperature of the reaction vessel reached 120° C., 2,7-octadienyl formate and a 20% by mass tricyclohexyl phosphine-o-xylene solution were added thereto at feed rates of 126.2 kg/h and 0.12 kg/h, respectively, using a feed pump. When the reaction was conducted while distilling off a reaction product containing the resulting octadiene out of the reaction system, it was possible to continue the reaction for 1,020 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 1,020 h were 128,700 kg (835.7 kmol) and 125.0 kg (80.4 mol in terms of tricyclohexyl phosphine), respectively. Also, a total amount of the resulting reaction distillate mixed solution was 86,700 kg, and a yield of the octadiene was 94.3%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 95/5. (The boiling point of trioctylamine as measured under atmospheric pressure was 365° C.)

Example 3

A 10 m³ reaction vessel was charged with 3,513 L (3,320 kg) of diethylene glycol dimethyl ether, 60.0 g (0.27 mol) of palladium acetate, 9.0 kg of a 20% by mass tricyclohexyl phosphine-o-xylene solution (5.8 mol in terms of tricyclohexyl phosphine) and 6.0 kg (17.0 mol) of trioctylamine, and the reaction pressure in the reaction vessel was reduced to 40 kPa and the reaction temperature therein was raised to 120° C. At the time at which an inside temperature of the reaction vessel reached 120° C., 2,7-octadienyl formate and a 20% by mass tricyclohexyl phosphine-o-xylene solution were added thereto at feed rates of 143.1 kg/h and 0.66 kg/h, respectively, using a feed pump. When the reaction was conducted while distilling off a reaction product containing the resulting octadiene out of the reaction system, it was possible to continue the reaction for 204 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 204 h were 29,192 kg (189.6 kmol) and 134.4 kg (86.4 mol in terms of tricyclohexyl phosphine), respectively. Also, a total amount of the resulting reaction distillate mixed solution was 19,780 kg, and a yield of the octadiene was 94.9%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 96/4.

Example 4

A 1-L three-necked flask was charged with 400 mL (378 g) of diethylene glycol dimethyl ether, 6.3 mg (0.03 mmol) of palladium acetate, 1.09 g of a 20% by mass tricyclohexyl phosphine-o-xylene solution (0.70 mmol in terms of tricyclohexyl phosphine) and 3.38 g (9.58 mmol) of trioctylamine, and the reaction pressure in the flask was reduced to 40 kPa and the reaction temperature therein was raised to 120° C. At the time at which an inside temperature of the flask reached 120° C., 2,7-octadienyl formate and a 20% by mass tricyclohexyl phosphine-o-xylene solution were added thereto at feed rates of 20.74 g/h and 0.28 g/h, respectively, using a feed pump. When the reaction was conducted while distilling off a reaction product containing the resulting octadiene out of the reaction system, it was possible to continue the reaction for 30 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 30 h were 622.14 g (4.04 mol) and 8.38 g (5.39 mmol in terms of tricyclohexyl phosphine), respectively. Also, a total amount of the resulting reaction distillate mixed solution was 413.71 g, and a yield of the octadiene was 93.1%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 96/4.

Example 5

The respective components were charged into the flask in the same manner as in Example 4 except for using 0.09 g (0.58 mmol) of triisopropyl phosphine in place of the 20% by mass tricyclohexyl phosphine-o-xylene solution, and the reaction pressure in the flask was reduced to 40 kPa and the reaction temperature therein was raised to 120° C. At the time at which an inside temperature of the flask reached 120° C., a mixed solution of 2,7-octadienyl formate and triisopropyl phosphine (containing 803.27 g of 2,7-octadienyl formate and 0.98 g of triisopropyl phosphine) was added thereto at a feed rate of 20.52 g/h using a feed pump. When the reaction was conducted while distilling off a reaction product containing the resulting octadiene out of the reaction system, it was possible to continue the reaction for 30 h.

Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. A total amount of the mixed solution of the 2,7-octadienyl formate and triisopropyl phosphine added in the continuous reaction for 30 h was 615.6 g (containing 614.85 g (3.99 mol) of 2,7-octadienyl formate and 0.75 g (4.69 mmol) of triisopropyl phosphine). Also, a total amount of the resulting reaction distillate mixed solution was 401.33 g, and a yield of the octadiene was 91.4%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 93/7.

Example 6

The respective components were charged into the flask in the same manner as in Example 4 except for using 0.12 g (0.60 mmol) of tri-n-butyl phosphine in place of the 20% by mass tricyclohexyl phosphine-o-xylene solution, and the reaction pressure in the flask was reduced to 40 kPa and the reaction temperature therein was raised to 120° C. At the time at which an inside temperature of the flask reached 120° C., a mixed solution of 2,7-octadienyl formate and tri-n-butyl phosphine (containing 800.78 g of 2,7-octadienyl formate and 1.28 g of tri-n-butyl phosphine) was added thereto at a feed rate of 20.95 g/h using a feed pump. When the reaction was conducted while distilling off a reaction product containing the resulting octadiene out of the reaction system, it was possible to continue the reaction for 30 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. A total amount of the mixed solution of the 2,7-octadienyl formate and tri-n-butyl phosphine added in the continuous reaction for 30 h was 628.5 g (containing 627.50 g (4.07 mol) of 2,7-octadienyl formate and 1.00 g (4.95 mmol) of tri-n-butyl phosphine). Also, a total amount of the resulting reaction distillate mixed solution was 405.67 g, and a yield of the octadiene was 90.6%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 95/5 to 90/10.

Example 7

The respective components were charged into the flask in the same manner as in Example 4 except for using mesitylene in place of the diethylene glycol dimethyl ether, and the reaction pressure in the flask was reduced to 40 kPa and the reaction temperature therein was raised to 120° C. At the time at which an inside temperature of the flask reached 120° C., 2,7-octadienyl formate and a 20% by mass tricyclohexyl phosphine-o-xylene solution were added thereto at feed rates of 20.68 g/h and 0.28 g/h, respectively, using a feed pump. When the reaction was conducted while distilling off a reaction product containing the resulting octadiene out of the reaction system, it was possible to continue the reaction for 30 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 30 h were 620.4 g (4.03 mol) and 8.40 g (5.40 mmol in terms of tricyclohexyl phosphine), respectively. Also, a total amount of the resulting reaction distillate mixed solution was 378.89 g, and a yield of the octadiene was 85.5%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 90/10.

Example 8

The respective components were charged into the flask in the same manner as in Example 4 except for using 2-octanone in place of the diethylene glycol dimethyl ether, and the reaction pressure in the flask was reduced to 40 kPa and the reaction temperature therein was raised to 120° C. At the time at which an inside temperature of the flask reached 120° C., 2,7-octadienyl formate and a 20% by mass tricyclohexyl phosphine-o-xylene solution were added thereto at feed rates of 20.36 g/h and 0.28 g/h, respectively, using a feed pump. When the reaction was conducted while distilling off a reaction product containing the resulting octadiene out of the reaction system, it was possible to continue the reaction for 30 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 30 h were 610.8 g (3.97 mol) and 8.46 g (5.44 mmol in terms of tricyclohexyl phosphine), respectively. Also, a total amount of the resulting reaction distillate mixed solution was 309.76 g, and a yield of the octadiene was 71.0%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 95/5 to 90/10.

Example 9

The respective components were charged into the flask in the same manner as in Example 4 except for using 1.65 g (9.59 mmol) of N,N,N',N'-tetramethyl-1,6-hexanediamine in place of the trioctylamine, and the reaction pressure in the flask was reduced to 40 kPa and the reaction temperature therein was raised to 120° C. At the time at which an inside temperature of the flask reached 120° C., 2,7-octadienyl formate and a 20% by mass tricyclohexyl phosphine-o-xylene solution were added thereto at feed rates of 20.68 g/h and 0.28 g/h, respectively, using a feed pump. When the reaction was conducted while distilling off a reaction product containing the resulting octadiene out of the reaction system, it was possible to continue the reaction for 30 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 30 h were 620.33 g (4.03 mol) and 8.33 g (5.36 mmol in terms of tricyclohexyl phosphine), respectively. Also, a total amount of the resulting reaction distillate mixed solution was 398.78 g, and a yield of the octadiene was 90.0%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 95/5.

Example 10

The respective components were charged into the flask in the same manner as in Example 4 except for using 1.66 g (9.57 mmol) of N,N,N',N'',N''-pentamethyl diethylenetriamine in place of the trioctylamine, and the reaction pressure in the flask was reduced to 40 kPa and the reaction temperature therein was raised to 120° C. At the time at which an inside temperature of the flask reached 120° C., 2,7-octadienyl formate and a 20% by mass tricyclohexyl phosphine-o-xylene solution were added thereto at feed rates of 21.05 g/h and 0.29 g/h, respectively, using a feed pump. When the reaction was conducted while distilling off a reaction product containing the resulting octadiene out of the reaction system, it was possible to continue the reaction for 30 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 30 h were 631.40 g (4.10 mol) and 8.58 g (5.52 mmol in terms of tricyclohexyl phosphine), respectively. Also, a total amount of the resulting reaction distillate mixed solution was 408.33 g, and a yield of the octadiene was 90.5%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 95/5.

Example 11

The respective components were charged into the flask in the same manner as in Example 4 except that the amounts of the diethylene glycol dimethyl ether and trioctylamine used therein were changed to 340 mL (321 g) and 50.00 g (141.64 mmol), respectively, and the reaction pressure in the flask was reduced to 40 kPa and the reaction temperature therein was raised to 120° C. At the time at which an inside temperature of the flask reached 120° C., 2,7-octadienyl formate and a 20% by mass tricyclohexyl phosphine-o-xylene solution were added thereto at feed rates of 20.95 g/h and 0.28 g/h, respectively, using a feed pump. When the reaction was conducted while distilling off a reaction product containing the resulting octadiene out of the reaction system, it was possible to continue the reaction for 30 h. Even when the reaction was further continued, an amount of a reaction distillate mixed solution produced was kept unchanged, and therefore the catalyst composition constituted of the palladium compound and the tertiary organophosphorus compound was able to maintain a catalytic activity thereof. Total amounts of the 2,7-octadienyl formate and 20% by mass tricyclohexyl phosphine-o-xylene solution added in the continuous reaction for 30 h were 628.45 g (4.08 mol) and 8.50 g (5.46 mmol in terms of tricyclohexyl phosphine), respectively. Also, a total amount of the resulting reaction distillate mixed solution was 412.00 g, and a yield of the octadiene was 91.8%. As a result of subjecting the reaction distillate mixed solution periodically sampled to GC analysis under the above conditions, it was confirmed that a ratio of an amount of 1,7-octadiene produced to an amount of 1,6-octadiene produced was in the range of from 97/3 to 95/5.

INDUSTRIAL APPLICABILITY

In accordance with the present invention, it is possible to produce an octadiene that is important as a crosslinking agent or a modifying agent used upon production of polyolefins as well as an intermediate product for synthesis of sebacic acid, C10 diols or C10 diamines in an industrially useful manner.

The invention claimed is:
1. A process for producing an octadiene, comprising:
continuously adding 2,7-octadienyl formate into a reaction system in which a mixture of a palladium compound, a tertiary organophosphorus compound, a tertiary amine and a solvent is present;
reacting the 2,7-octadienyl formate to produce a reaction product comprising octadiene; and
continuously distilling off the reaction product out of the reaction system.
2. The process according to claim 1, wherein the tertiary amine is present in an amount of from 0.0001 to 95% by mass on the basis of a total amount of the mixture of the palladium compound, the tertiary organophosphorus compound, the tertiary amine and the solvent which is present in the reaction system.
3. The process according to claim 1, wherein the tertiary amine has a boiling point higher than a boiling point of the octadiene as measured under atmospheric pressure.
4. The process according to claim 1, wherein the tertiary organophosphorus compound is present in an amount of from 4 to 10,000 times mol, on the basis of a palladium atom in the palladium compound.
5. The process according to claim 1, wherein the solvent has a boiling point higher than a boiling point of the octadiene as measured under atmospheric pressure.
6. The process according to claim 5, wherein the solvent is an ether-based solvent.

* * * * *